Dec. 6, 1960 E. S. BOERNER Plant Pat. 1,997
CHRYSANTHEMUM PLANT
Filed Feb. 26, 1960
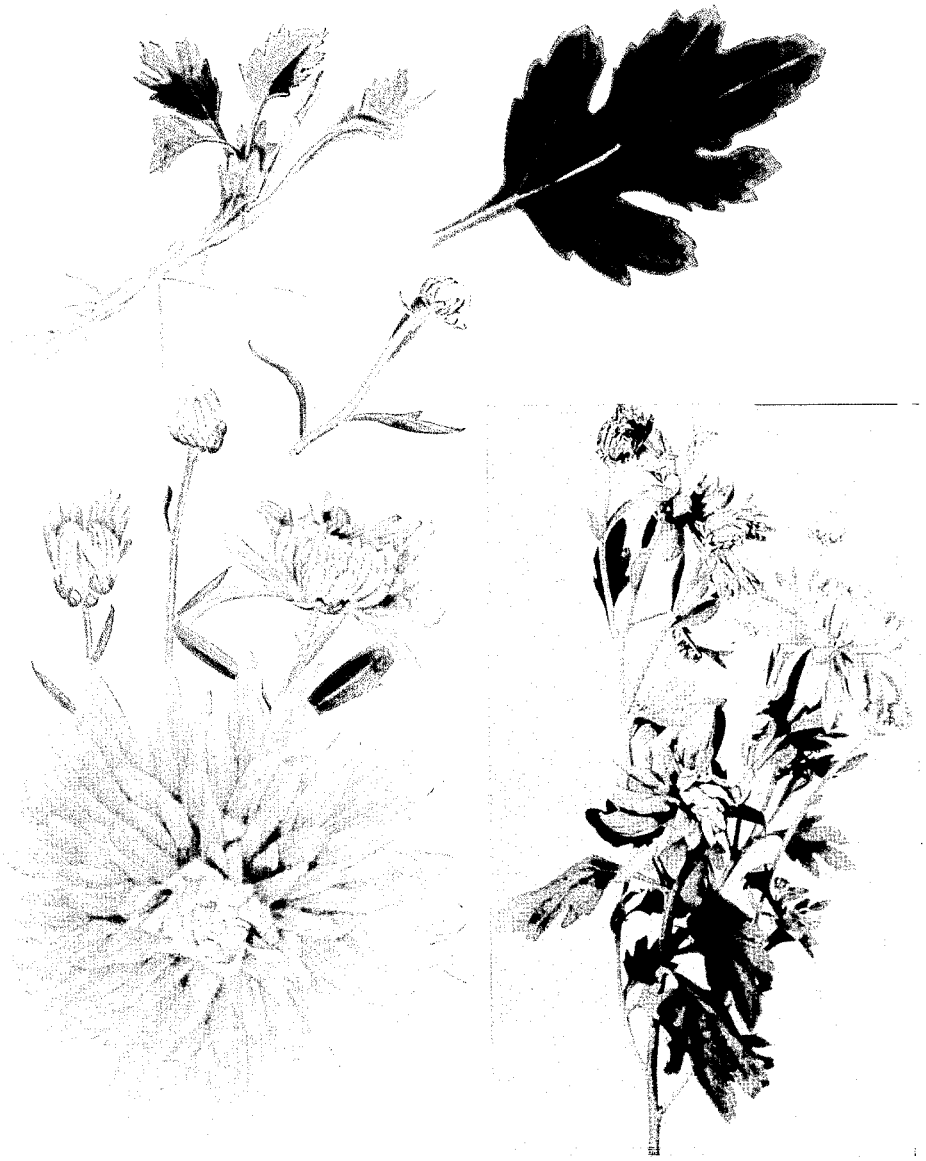
Inventor.
E. S. Boerner
By: Robb & Robb
Attorneys.

United States Patent Office

Plant Pat. 1,997
Patented Dec. 6, 1960

1,997

CHRYSANTHEMUM PLANT

Eugene S. Boerner, Newark, N.Y., assignor to Jackson & Perkins Company, Newark, N.Y., a corporation of New York Filed Feb. 26, 1960, Ser. No. 11,395

1 Claim. (Cl. 47—60)

The present invention relates to a new and distinct variety of chrysanthemum plant of the decorative class, which was originated by me by crossing the variety "Thrasher" (Plant Patent No. 1,553) with the variety "Wood Peewee" (Plant Patent No. 1,824).

The primary objective of this breeding was to produce a new chrysanthemum variety having a flower color corresponding to that of the parent variety "Thrasher," combined with a plant strength and hardiness corresponding to that of the parent variety "Wood Peewee." This objective was fully achieved, along with other desirable improvements, as evidenced by the following characteristics which are outstanding in the new variety and which distinguish it from its parents, as well as from all other varieties of which I am aware:

(1) Good plant strength and hardiness;
(2) An early blooming habit;
(3) Exceptionally good floriferousness; and
(4) A general color tonality of the flowers corresponding to Scarlet, lightly overcast with Scarlet Red.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen plant which is depicted in black-and-white for the purpose of illustrating the form and habit of growth of the plant.

The following is a detailed description of the new variety, with color terminology in accordance with Ridgway's Color Standards and Nomenclature, as based upon observations made from specimens grown outdoors at Newark, New York, near mid-afternoon during the middle of the month of October:

Parentage: Seedling.
*Seed parent.*—"Thrasher."
*Pollen parent.*—"Wood Peewee."

Classification: Decorative.
Growth: Vigorous; tall (attains height of from 30 to 36 inches).
Cold resistance: Plants are very winter hardy in northern New York; burn slightly with late frosts.
Blooming period: In the Newark, New York climatic area, average date of commencement of bloom is late September, with blooms continuing to frost.

*Flower*

Bud:
*Color.*—When sepals first divide—Primrose Yellow, Plate 30, lightly overcast with Pale Flesh Color, Plate 14. When petals begin to unfurl—Light Jasper Red, Plate 13, lightly overcast with Capucine Buff, Plate 3. When half-brown: inside of petals—Jasper Red, Plate 13, lightly overcast with Pale Orange-Yellow, Plate 3; outside of petals—Pale Orange-Yellow, Plate 3, lightly overcast with Strawberry Pink, Plate 1.
*Peduncle.*—Color—Absinthe Green, Plate 31. Strength—strong.

Bloom:
*Size.*—From 4½ to 5 inches.
*Stem.*—Strong.
*Form.*—Decorative; very floriferous.
*Petalage.*—Double.
*Color.*—Center of flower—Light Orange-Yellow, Plate 3. Outer petals—Jasper Red, Plate 13, lightly overcast with Peach Red, Plate 1. Base of petals—Dull Green-Yellow, Plate 17. Inside of petals—Scarlet, Plate 1, lightly overcast with Scarlet Red, Plate 1. Reverse of petals—Pale Orange-Yellow, Plate 3.
*Petals.*—Texture—medium. Form—oval.
*Fragrance.*—Characteristic chrysanthemum.

*Plant*

Form: Upright; mound type.
Growth: Free; vigorous.
Foliage:
*Size.*—Medium.
*Quantity.*—Normal.
*Color.*—Upper side—Varley's Green, Plate 18. Under side—Bice Green, Plate 17.
*Texture.*—Leathery.

I claim:

A new and distinct variety of chrysanthemum plant of the decorative class, substantially as herein shown and described, characterized particularly as to novelty by the unique combination of good plant strength and hardiness, an early blooming habit, exceptionally good floriferousness, and a distinctive Scarlet, lightly overcast with Scarlet-Red general color tonality of the flowers.

No references cited.